United States Patent
Taormina et al.

(10) Patent No.: US 6,578,576 B1
(45) Date of Patent: Jun. 17, 2003

(54) MEDICAL TUBE HOLDER

(76) Inventors: Salvatore A. Taormina, 902 Simmons La., Novato, CA (US) 94945; Anthony M. Taormina, 204 Wishkah La., Petaluma, CA (US) 94954

( * ) Notice: Subject to any disclaimer, the term of this patent is extended or adjusted under 35 U.S.C. 154(b) by 29 days.

(21) Appl. No.: 09/840,659

(22) Filed: Apr. 23, 2001

Related U.S. Application Data

(60) Provisional application No. 60/200,245, filed on Apr. 28, 2000.

(51) Int. Cl.[7] ............................................. A61M 16/00
(52) U.S. Cl. ........................... 128/207.17; 128/207.14; 128/200.24
(58) Field of Search ................... 128/207.17, DIG. 26, 128/206.17, 207.11, DIG. 15, 204.11, 207.14

(56) References Cited

U.S. PATENT DOCUMENTS

| | | | |
|---|---|---|---|
| 3,977,407 A | 8/1976 | Coleman et al. | |
| 4,592,351 A | 6/1986 | Smith et al. | |
| 4,906,234 A | 3/1990 | Voychehovski | |
| 5,117,818 A | 6/1992 | Palfy | |
| 5,295,480 A | * 3/1994 | Zemo | 128/207.17 |
| 5,395,343 A | 3/1995 | Iscovich | |
| 5,437,273 A | 8/1995 | Bates et al. | |
| 5,533,506 A | * 7/1996 | Wood | 128/207.18 |
| 5,555,881 A | * 9/1996 | Rogers et al. | 128/207.17 |
| 5,626,565 A | 5/1997 | Landis et al. | |
| 5,653,228 A | * 8/1997 | Byrd | 128/207.11 |
| 5,699,787 A | 12/1997 | Thompson | |
| 5,894,840 A | 4/1999 | King | |
| 5,934,276 A | 8/1999 | Fabro et al. | |
| 6,050,263 A | 4/2000 | Choksi et al. | |
| 6,408,850 B1 | * 6/2002 | Sudge | 128/207.17 |

* cited by examiner

*Primary Examiner*—Henry Bennett
*Assistant Examiner*—Nihir Patel
(74) *Attorney, Agent, or Firm*—Jack Lo

(57) ABSTRACT

The present medical tube holder is comprised of a base member, a pair of strap anchors pivotally attached to opposite ends of the base member, a strap connected between the strap anchors, and a clip movably attached to the base member. The ends of the base member are curved upwardly to align with the top of the ears. The strap anchors are pivoted to self-adjust to individual patients. The strap has a cotton inner side for comfort, and hook-and-loop ends for adjusting its length. A bracket behind the clip is engaged on the base member to allow the clip to slide side-to-side along the base member for alignment with either nostril.

19 Claims, 2 Drawing Sheets

MEDICAL TUBE HOLDER

CROSS REFERENCE TO RELATED APPLICATIONS

We claim the benefit of a provisional application with Ser. No. 60/200,245 which was filed on Apr. 28, 2000.

BACKGROUND OF THE INVENTION

1. Field of the Invention

This invention relates generally to tracheal and gastric tube holders.

2. Prior Art

Medical tubes such as nasal-tracheal and nasal-gastric tubes are used for a variety of procedures, including gastric and airway interventions. A medical tube is typically secured with tape applied near the nose, but the tape tends to irritate the skin after prolonged use. The tape is also prone to loosening due to secretions from the patient, such as blood, vomit, and perspiration, and other types of moisture, such as rain. Removing the tape is usually painful. The tape may have to be changed if it is failing, if it is dirty, or if the tube has to be moved from one nostril to the other. The use of tape to secure a medical tube is generally very undesirable.

Various holders are known among the prior art for securing medical tubes with straps instead of tape. A typical holder is comprised of a clip attached to a base member, and a head strap attached to the sides of the base member. Although some have clips which are adjustable for holding tubes of different diameters, the clips are difficult to adjust, and some clips cannot be easily loosened after they are tightened. They all have straps which are attached to the base members at a fixed angle that cannot suit all patients. Some of the nasal tube holders have clips which are movable to different distinct positions on the base member for aligning with either nostril, but inconveniently, the clips must be separated from and reattached to the base member to change position.

OBJECTIVES OF THE INVENTION

The objectives of the present medical tube holder are:

to securely hold a medical tube in the nose of a patient;

to have a base member with ends which are curved to align with the ears;

to have a strap which pivots to fit different patients;

to have a clip which is adjustable for holding tubes of different sizes;

to have a clip which is easy to tighten and loosen;

to have a clip which is easily adjustable side-to-side on the base member; and to have a clip which is angled for holding the tube closer to and in angular alignment with the nostril for better comfort and security.

Further objectives of the present invention will become apparent from a consideration of the drawings and ensuing description.

BRIEF SUMMARY OF THE INVENTION

The present medical tube holder is comprised of a base member, a pair of strap anchors pivotally attached to opposite ends of the base member, a strap connected between the strap anchors, and a clip movably attached to the base member. The ends of the base member are curved upwardly to align with the top of the ears. The strap anchors are pivoted to self-adjust to individual patients. The strap has a cotton inner side for comfort, and hook-and-loop ends for adjusting its length. A bracket behind the clip is engaged on the base member to allow the clip to slide side-to-side along the base member for alignment with either nostril.

Figure 1:
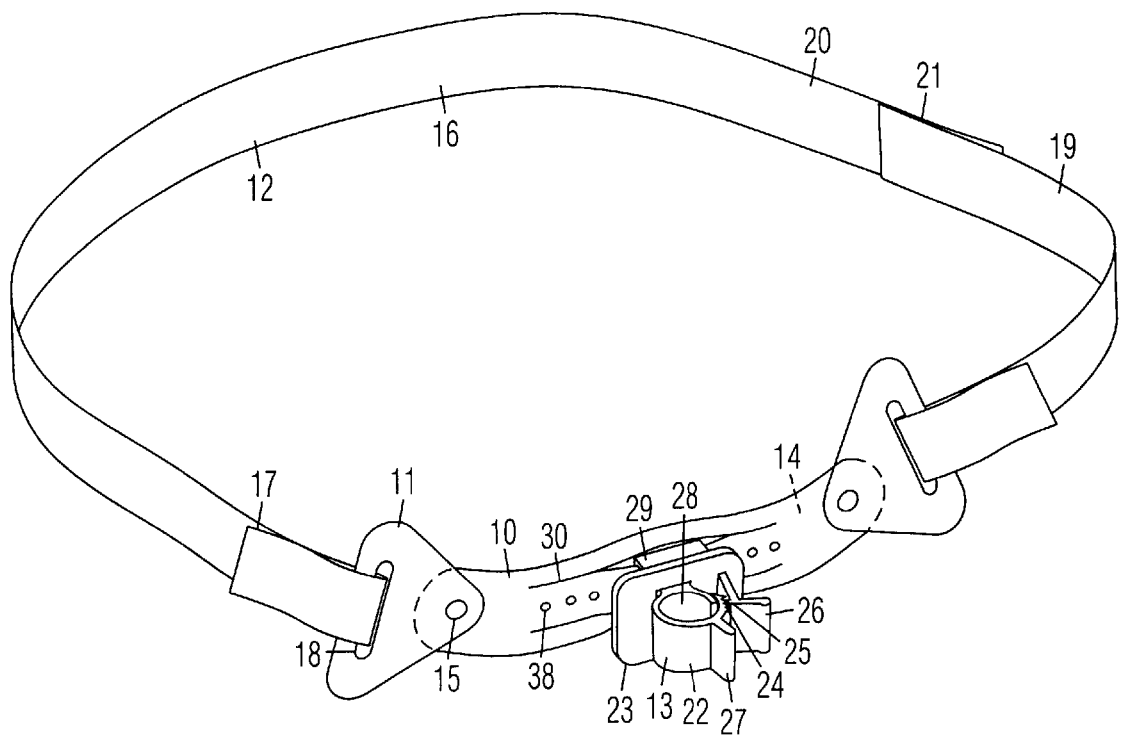
FIG. 1 is a front perspective view of the present medical tube holder.

| DRAWING REFERENCE NUMERALS | |
|---|---|
| 10. Base Member | 11. Strap Anchors |
| 12. Strap | 13. Clip |
| 14. Rubbery Material | 15. Pivot |
| 16. Cotton | 17. Hook-and-Loop |
| 18. Slot | 19. Strap Section |
| 20. Strap Section | 21. Hook-and-Loop |
| 22. Loop | 23. Plate |
| 24. Teeth | 25. Pin |
| 26. Lever | 27. Handle |
| 28. Rubbery Material | 29. Bracket |
| 30. Slits | 31. Tube |
| 32. Clip | 33. Loop |
| 34. Plate | 35. Wedge |
| 36. Tube | 37. Bracket |
| 38. Detents | |

DETAILED DESCRIPTION OF THE INVENTION

FIGS. 1–2

Figure 2:
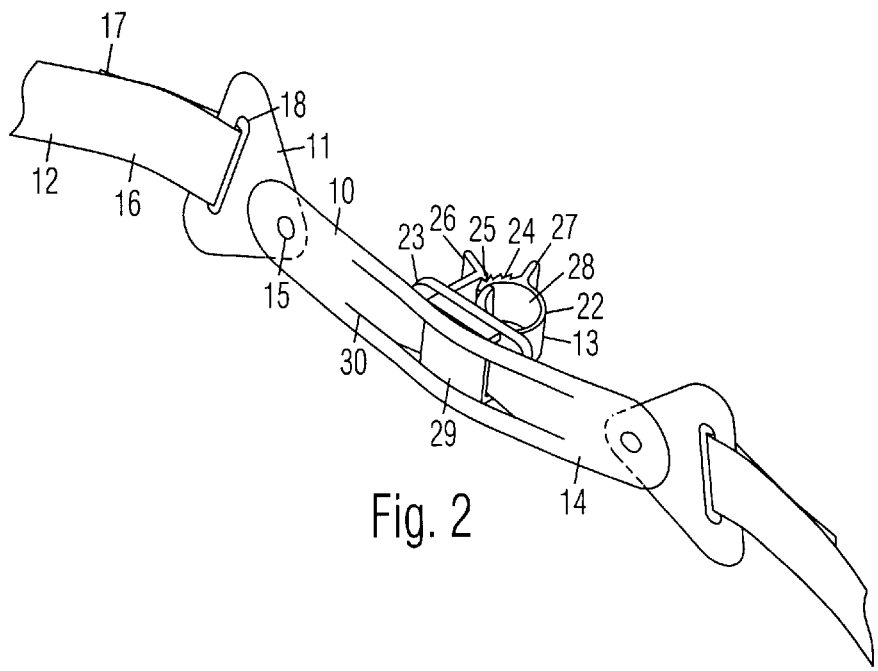
FIG. 2 is a rear perspective view thereof.

A preferred embodiment of the present medical tube holder is shown in front and rear perspective views in FIGS. 1 and 2. It is comprised of an elongated base member 10, a pair of strap anchors 11 pivotally attached to opposite ends of base member 10, a strap 12 connected between strap anchors 11, and a clip 13 movably attached to base member 10. The ends of base member 10 are curved upwardly, and the back is provided with a rubbery material 14 for resisting slipping. Base member 10 is preferably made of a flexible plastic. Strap anchors 11 are preferably triangular, and are attached to respective ends of base member 10 with pivots 15 through their inner corners. Strap 12 preferably has a cotton inner side 16 for comfort, and hook-and-loop opposite ends 17 looped through slots 18 along straight edges of strap anchors 11 for length adjustment. Strap 12 is preferably comprised of two separate sections 19 and 20 connected together by hook-and-loop fasteners 21 for easy length adjustment. Alternatively, strap anchors 11 may be eliminated and strap 12 may be attached directly to base member 10. Clip 13 is comprised of a springy loop 22 attached to a plate 23 for holding a medical tube (not shown). Ratchet teeth 24 are provided on one end of loop 22. A pin 25 on a springy lever 26 with one end attached to plate 23 is biased against ratchet teeth 24 to hold loop 22 in any selected position. A handle 27 is attached to loop 22 adjacent ratchet teeth 24. Loop 22 is tightened by squeezing lever 26 and handle 27 together to advance teeth 24 past pin 25. Loop 22 is loosened by spreading apart lever 26 and handle 27 to disengage lever 26 from loop 22. A rubbery material 28 is provided on the inside of loop 22 for securely holding the medical tube. A bracket 29 behind plate 23 is engaged in parallel slits 30 on base member 10 and allows clip 13 to move side-to-side along base member 10. Clip 13 is maintained in its selected position by detents 38 along base member 10. Alternatively, bracket 29 may be of another shape, such as a "T" shape for riding in a single slit on base member 10, two opposed "L" shapes, etc. Also, slits 30 may be eliminated and bracket 29 may be wrapped entirely around or fixedly attached to base member 10.

FIG. 3

Figure 3:
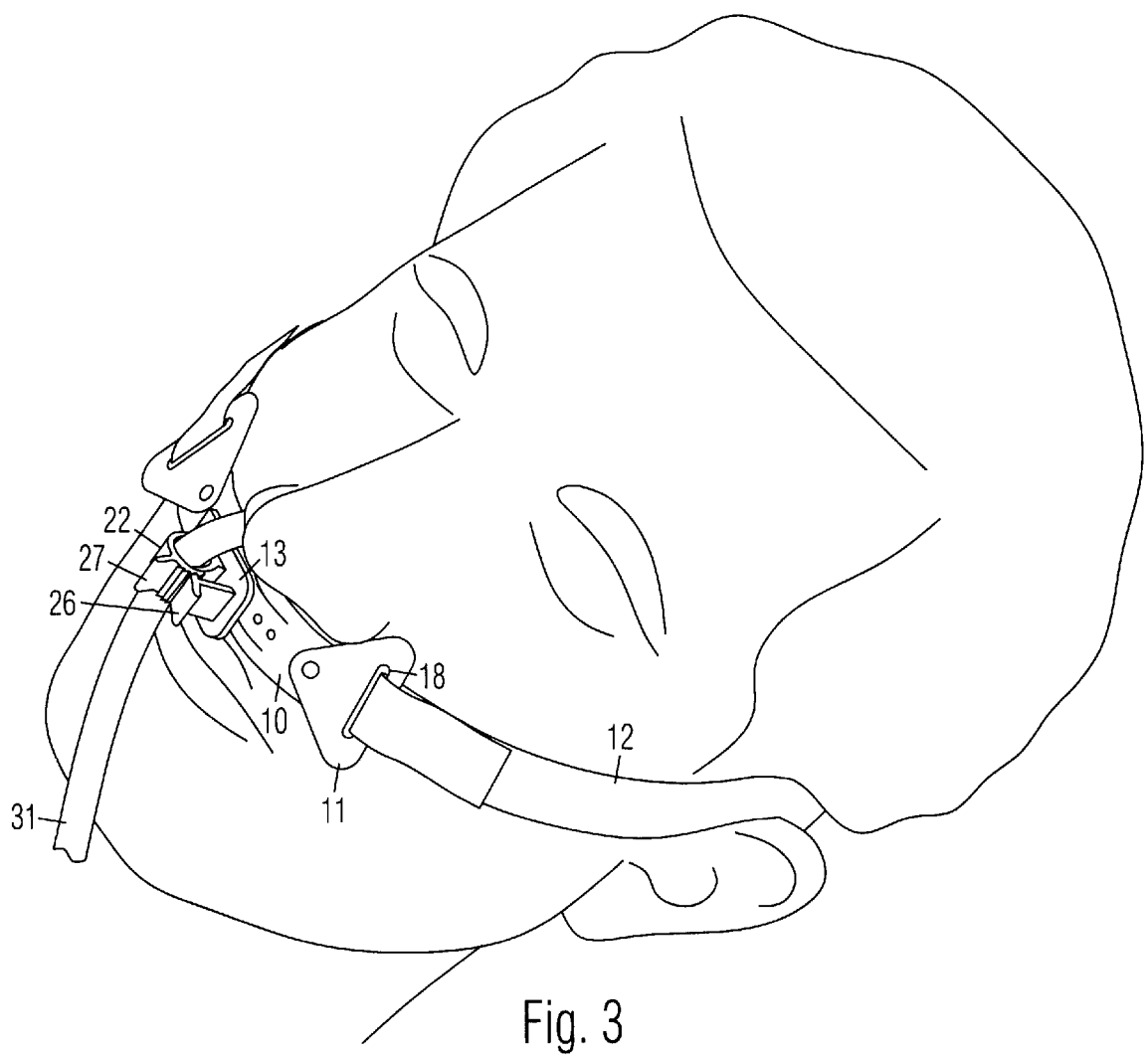
FIG. 3 is a front perspective view thereof on a patient.

The medical tube holder is shown worn on a patient in FIG. 3. When used to hold a nasal tube 31 as shown, base member 10 is positioned between the upper lip and the nose. The holder can also be used to secure an oral tracheal tube by positioning it under the lower lip on the chin. In either case, its upwardly curved ends are generally aligned with the tops of the ears. Strap 12 is wrapped around the head and supported at the tops of the ears. The separable sections of strap 12 are disconnected to be positioned around the head and reconnected to secure the tube holder in position. The ends of strap 12 may be slid through slots 18 in strap anchors II to tighten or loosen strap 12, or the separable sections may be separated and reconnected to adjust the fit. If the ends of base member 10 are not sufficiently aligned with the tops of the ears, any angular difference would be accommodated by pivoting strap anchors 11 which automatically pivots to a suitable position for the greatest comfort. Base member 10 is prevented from slipping by its rubbery back.

Nasal tube 31 or any other tube is installed by inserting it into the patient, spreading apart lever 26 and handle 27 to open up loop 22, positioning the tube into loop 22, and squeezing lever 26 and handle 27 together to tighten loop 22 against the tube. Clip 13 may thus be easily loosened and tightened again for repositioning or replacing the tube. A significant advantage provided by clip 13 is that it can also be easily slid sideways to align with either nostril to position the tube in either nostril without having to detach and reattach it.

FIG. 4

Figure 4:
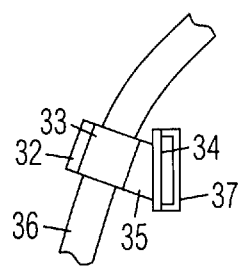
FIG. 4 is a side view of an alternative clip thereof.

An alternative clip 32 is shown in a side view in FIG. 4. It is comprised of a loop 33 attached to a plate 34 by a wedge 35, so that the axis of loop 33 is angled relative to plate 34 for better aligning a medical tube 36 with the angle of the nostril. A bracket 37 behind plate 34 is for attaching to the base member (not shown).

SUMMARY AND SCOPE

Although the foregoing description is specific, it should not be considered as a limitation on the scope of the invention, but only as an example of the preferred embodiment. Many variations are possible within the teachings of the invention. For example, the medical tube holder may be made in different sizes, such as adult and child sizes. It is preferably made of latex-free materials to avoid causing reactions in patients with latex allergies. Different attachment methods, fasteners, materials, dimensions, etc. can be used unless specifically indicated otherwise. The relative positions of the elements can vary, and the shapes of the elements can vary. Therefore, the scope of the invention should be determined by the appended claims and their legal equivalents, not by the examples given.

We claim:

1. A medical tube holder, comprising:
   an elongated base member adapted to be positioned transversely under a nose of a patient;
   a pair of strap anchors pivotally attached to opposite ends of said base member;
   a strap connected between said strap anchors and adapted to be wrapped around a head of said patient; and
   a clip movably attached to said base member with a bracket for holding a medical tube inserted into said patient, said clip is infinitely adjustable side-to-side along said base member for aligning said medical tube with either nostril when said medical tube is inserted into a nose of said patient.

2. The medical tube holder of claim 1, wherein said ends of said base member are fixedly curved upwardly and adapted to be aligned with respective ears of said patient.

3. The medical tube holder of claim 1, wherein said strap has a cotton inner side for comfort, and hook-and-loop opposite ends looped through slots in said strap anchors for length adjustment.

4. The medical tube holder of claim 1, wherein said strap is comprised of two separate sections connected together by hook-and-loop fasteners for length adjustment.

5. The medical tube holder of claim 1, wherein said clip is maintained in any selected position by detents along said base member.

6. The medical tube holder of claim 1, further including a wedge connecting said to clip to said base member at a predetermined angle substantially less than a right angle to align an axis of said loop with a nostril of said patient for better comfort and security.

7. A medical tube holder, comprising:
   an elongated base member adapted to be positioned transversely under a nose of a patient;
   a pair of strap anchors pivotally attached to opposite ends of said base member;
   a strap connected between said strap anchors and adapted to be wrapped around a head of said patient;
   a slit extending along said base member; and
   a clip movably attached to said base member with a bracket positioned in said slit, wherein said clip is adapted to hold a medical tube inserted into said patient, said clip is infinitely adjustable side-to-side along said slit in said base member for aligning said medical tube with either nostril when said medical tube is inserted into a nose of said patient.

8. The medical tube holder of claim 7, wherein said ends of said base member are fixedly curved upwardly and adapted to be aligned with respective ears of said patient.

9. The medical tube holder of claim 7, wherein said strap has a cotton inner side for comfort, and hook-and-loop opposite ends looped through slots in said strap anchors for length adjustment.

10. The medical tube holder of claim 7, wherein said strap is comprised of two separate sections connected together by hook-and-loop fasteners for length adjustment.

11. The medical tube holder of claim 7, wherein said clip is maintained in any selected position by detents along said base member.

12. The medical tube holder of claim 7, further including a wedge connecting said clip to said base member at a predetermined angle substantially less than a right angle to align an axis of said loop with a nostril of said patient for better comfort and security.

13. A medical tube holder, comprising:
   an elongated base member adapted to be positioned transversely under a nose of a patient;
   a pair of strap anchors pivotally attached to opposite ends of said base member;
   a strap connected between said strap anchors and adapted to be wrapped around a head of said patient; and
   a clip movably attached to said base member with a bracket for holding a medical tube inserted into said patient, said clip is infinitely adjustable side-to-side along said base member for aligning said medical tube with either nostril when said medical tube is inserted into a nose of said patient.

wherein said clip is comprised of:
- a plate attached to said bracket;
- a springy loop attached to said plate;
- ratchet teeth at one end of said loop;
- a springy lever with one end attached to said plate;
- a pin on said lever biased against ratchet teeth to hold said loop in any selected position; and
- a handle attached to said loop, said loop is tightened when said lever and said handle are squeezed together to advance said teeth past said pin, and said loop is loosened when said lever and said handle are spread apart to disengage said lever from said loop.

14. The medical tube holder of claim 13, wherein said ends of said base member are fixedly curved upwardly and adapted to be aligned with respective ears of said patient.

15. The medical tube holder of claim 13, wherein said strap has a cotton inner side for comfort, and hook-and-loop opposite ends looped through slots in said strap anchors for length adjustment.

16. The medical tube holder of claim 13, wherein said strap is comprised of two separate sections connected together by hook-and-loop fasteners for length adjustment.

17. The medical tube holder of claim 13, wherein said clip is maintained in any selected position by detents along said base member.

18. The medical tube holder of claim 13, further including a wedge connecting said clip to said base member at a predetermined angle substantially less than a right angle to align an axis of said loop with a nostril of said patient for better comfort and security.

19. The medical tube holder of claim 13, further including a rubbery material arranged inside said loop for securely holding said medical tube.

* * * * *